(12) United States Patent
Ben-Nun

(10) Patent No.: US 7,585,295 B2
(45) Date of Patent: Sep. 8, 2009

(54) THERMAL AIRFLOW TOOL AND SYSTEM

(75) Inventor: Joshua Ben-Nun, Moshav Beit Herut (IL)

(73) Assignee: Itos International Ltd., Wanchai (HK)

( * ) Notice: Subject to any disclaimer, the term of this patent is extended or adjusted under 35 U.S.C. 154(b) by 365 days.

(21) Appl. No.: 11/019,125

(22) Filed: Dec. 22, 2004

(65) Prior Publication Data
US 2005/0154384 A1 Jul. 14, 2005

Related U.S. Application Data

(60) Provisional application No. 60/531,629, filed on Dec. 23, 2003.

(51) Int. Cl.
*A61B 18/18* (2006.01)
(52) U.S. Cl. .......................................... 606/28; 606/49
(58) Field of Classification Search ............. 606/27–31, 606/41, 48–50; 219/121.11, 121.6
See application file for complete search history.

(56) References Cited

U.S. PATENT DOCUMENTS

| | | | |
|---|---|---|---|
| 4,722,340 A * | 2/1988 | Takayama et al. ............... | 601/4 |
| 4,766,897 A | 8/1988 | Smirmaul | |
| 4,932,952 A * | 6/1990 | Wojciechowicz, Jr. ........ | 606/49 |
| 5,207,675 A * | 5/1993 | Canady ......................... | 606/40 |
| 5,269,787 A | 12/1993 | Cozean, Jr. et al. | |
| 5,620,440 A * | 4/1997 | Heckele et al. ................. | 606/28 |
| 5,720,745 A * | 2/1998 | Farin et al. ..................... | 606/49 |
| 5,730,742 A * | 3/1998 | Wojciechowicz ............ | 606/49 |
| 5,817,092 A * | 10/1998 | Behl ........................... | 606/41 |
| 5,873,883 A | 2/1999 | Cozean, Jr. et al. | |
| 5,964,752 A * | 10/1999 | Stone ........................... | 606/27 |
| 6,066,138 A | 5/2000 | Sheffer et al. | |
| 7,004,939 B2 * | 2/2006 | Mackay ....................... | 606/40 |

* cited by examiner

*Primary Examiner*—Michael Peffley
(74) *Attorney, Agent, or Firm*—Edward Langer, Adv.; Shibolet & Co.

(57) ABSTRACT

A combination pressurized airflow and thermal cutting tool constructed as a dual-use thermal airflow tool for directed heating and drying of a specific area in surgical procedures, such as, by way of example, in eye cataract surgery where it is primarily used for needs related to the operation of a thermal cutting tool. The thermal airflow tool comprises a probe having an elongated, hollow body adapted to provide electrical power to a burning ring formed at a distal end thereof, and an air channel for conducting pressurized airflow to the distal end of the probe, with at least two apertures radially disposed at the distal end of the probe. The thermal airflow tool is in physical and electrical connection with an air pressure unit and thermal power unit, respectively, for directing and concentrating at least one of the pressurized airflow and heat at the distal end of the thermal airflow tool onto a surgical area when electrical power is applied to the thermal airflow tool.

18 Claims, 10 Drawing Sheets

THERMAL AIRFLOW TOOL AND SYSTEM

This application claims priority to US Provisional Application 60/531,629 filed on Dec. 23, 2003.

FIELD OF THE INVENTION

The present invention relates generally to medical devices and systems, and more particularly to a thermal airflow tool and an associated system for improving theremal surgical procedure.

BACKGROUND OF THE INVENTION

Thermal surgical procedure is improved and made more efficient by concentrating heat at a position proximate to a surgical site. In eye cataract surgery, for example, the thermal procedure is usually complicated by the need for multiple instruments: a cutting tool, an air pressure inlet, a water pressure inlet, and related surgical and electrical equipment. It would be useful to simplify such surgical procedures by providing a combination tool that concentrates heat on the surgical site and which is constructed so as to be convenient to handle and which can be used for providing both regulated heating and airflow pressure directed to a surgical site.

SUMMARY OF THE INVENTION

Accordingly, it is a principal object of the present invention to overcome the disadvantages of the prior art and to provide a combination pressurized airflow and thermal cutting tool and an associated system. The airflow and thermal cutting tool, hereinafter thermal airflow tool of the present invention, is a dual-use tool for directed heating and drying of a specific area in surgical procedures, such as, by way of example, in eye cataract surgery where it is primarily used for needs related to the operation of a thermal cutting tool.

Thus there is provided a thermal airflow tool for performing a thermal surgical procedure, the thermal airflow tool comprising:

a probe comprising:

an elongated, hollow body adapted to provide electrical power to a burning ring formed at a distal end thereof;

an air channel for conducting pressurized airflow to the distal end of the probe;

at least two apertures radially disposed at the distal end of the probe in a non-perpendicular plane in respect to the axis of the hollow body for release of pressurized airflow, the air channel and the at least two apertures being in physical communication with one another within the hollow body of the probe; and an input connector mounted on a proximal end of the probe for connecting the probe with respective sources of electrical power and pressurized airflow, the input connector having at least one resistor for controlling and monitoring the electrical power provided to the burning ring.

There is also provided a thermal airflow system comprising:

an air pressure unit for providing pressurized airflow having substantially linear characteristics;

a thermal power unit for providing electrical power to the system; and a thermal airflow tool in physical and electrical connection to the air pressure unit and the thermal power unit, respectively, for directing and concentrating at least one of the pressurized airflow and heat at the distal end of the thermal airflow tool onto a surgical area when electrical power is applied to the thermal airflow tool.

The thermal airflow tool, in one embodiment of the invention, is provided with a burn-out resistor which functions as a fuse to limit the heating time in accordance with a predetermined temperature setting referenced to the size orifice needed in the thermal procedure. When the temperature has been reached, the burn-out resistor breaks the circuit and the heating element is turned off. The thermal airflow tool in this embodiment is for one-time use and is constructed as a disposable plug-in unit.

In another embodiment of the invention, the thermal airflow tool is provided with a fixed resistor of about 1000 ohms enabling repeated use of the thermal airflow tool for burning an orifice with a pre-set diameter in eye capsulotomy surgery.

Other features and advantages of the invention will become apparent from the following drawings and descriptions.

BRIEF DESCRIPTION OF THE DRAWINGS

For a better understanding of the invention in regard to the embodiments thereof, reference is made to the following drawings, not shown to scale, in which like numerals and letters designate corresponding sections or objects throughout, and in which.

DETAILED DESCRIPTION OF THE INVENTION

The present invention provides a system for surgical thermal procedures, such as for capsulotomy in eye cataract surgery, and a dual-purpose thermal airflow tool generally useful in this as well as in other kinds of surgical procedures. The system comprises two main parts, an air pressure unit and a thermal power unit connected to a thermal airflow tool.

Figure 1:
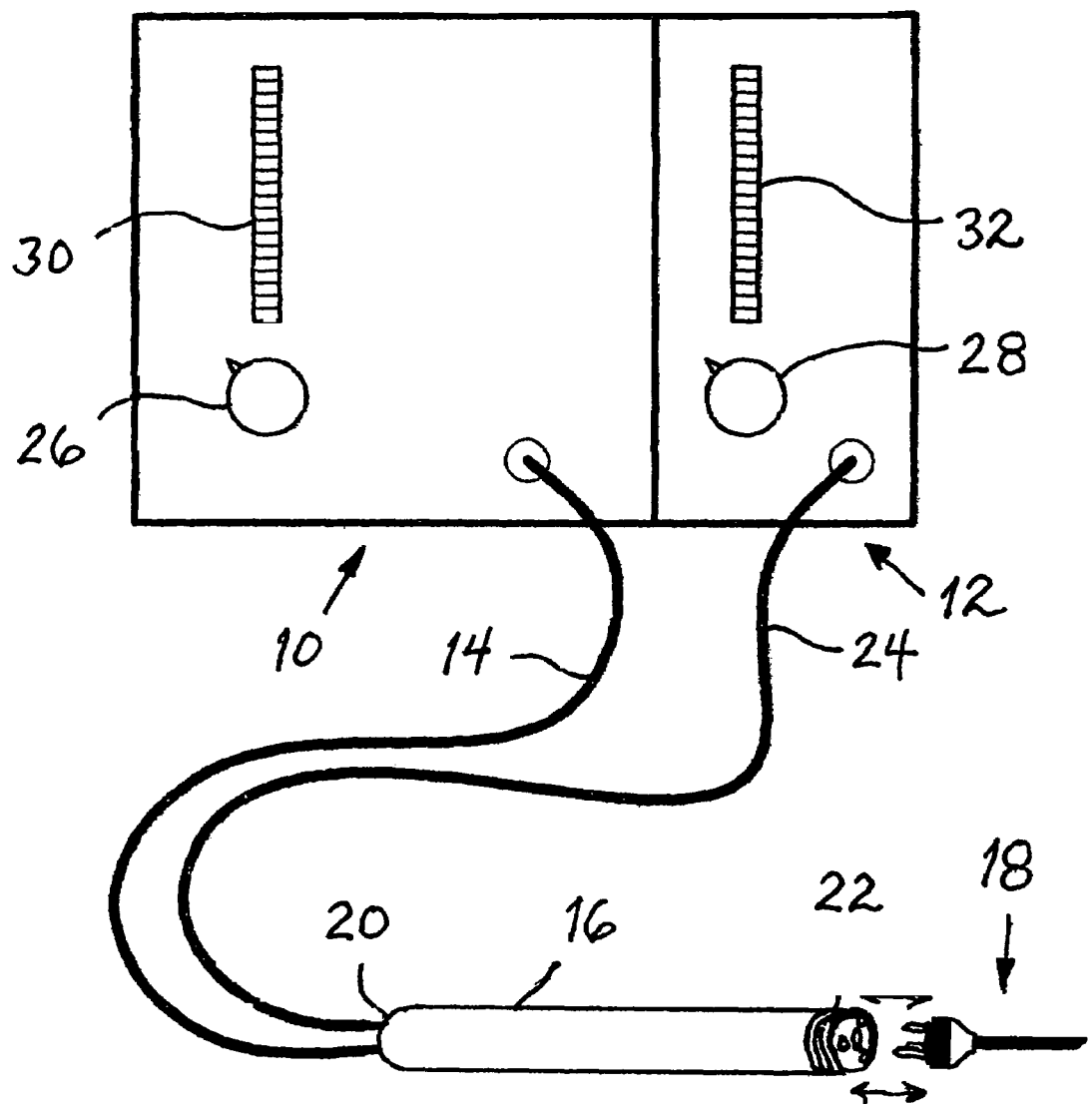
FIG. 1 is a general view of the layout of the major components comprising the system of the invention in accordance with an embodiment thereof.
Figure 2:
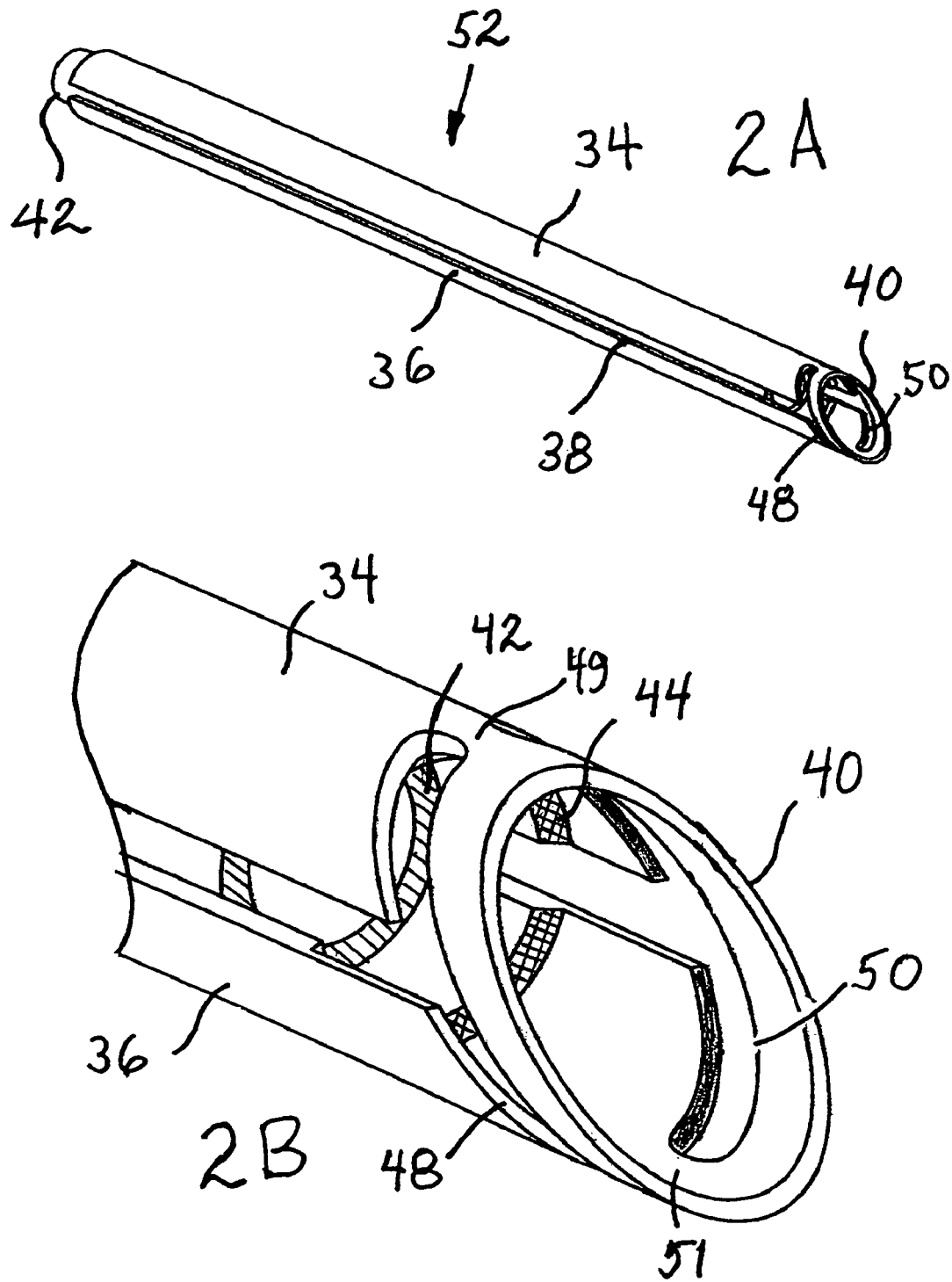
FIGS. 2A and 2B are isometric views of the probe of the thermal airflow tool of FIG. 1 and an enlarged, detailed view of a burning ring in accordance with the principles of the present invention, respectively.
Figure 3:
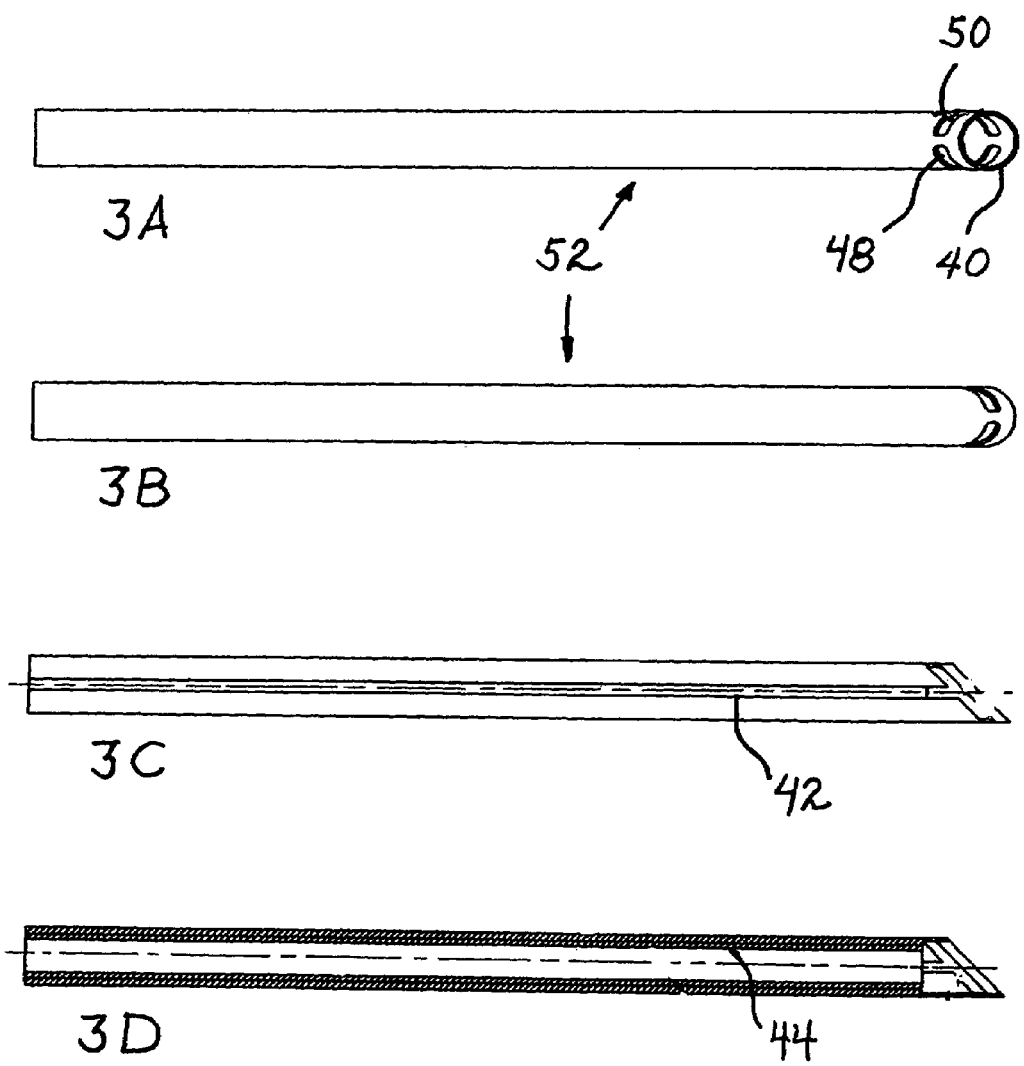
FIGS. 3A-D are orthographic views of the hollow tube construction of the probe, and axial cross-sections showing the construction of air pressure release apertures.

Referring now to FIG. 1, there is shown a general view of the layout of the major components comprising the system of the invention in accordance with an embodiment thereof. An air pressure unit 10 provides pressurized air for the system, while a thermal power unit 12 provides regulated heating, suitable, for example, for safely performing capsulotomy in eye cataract surgery (see FIG. 9). An air pressure input pipe 14 passes through a hollow handle 16 and directs airflow into thermal airflow tool 18 along a tube (see FIG. 2) passing through the central axis of both handle 16 and thermal airflow tool 18 when joined, as by example, with matching connectors, as is known by those skilled in the art, so as to direct a controlled stream of this pressurized air onto the surface of a surgical site. In the example shown in FIG. 1, the electrical connection to thermal unit 12 is by a three-wire power cable 24 wired from thermal power unit 12 to receptacle 22 disposed in the distal end of handle 16.

Individual foot-pedal switches (see FIG. 8) turn the power on/off to both units 10, 12 of the system, while controls 26 and 28 on each of the respective air pressure unit 10 and thermal power unit 12 allow a scaled adjustment and fine-tuning control of air and heating requirements, respectively, such as burning time, while individual bar graph displays 30, 32 provide a user with visual representations of the respective air pressure and heating levels being provided closest to the surgical site at the distal end of the thermal airflow tool 18.

FIGS. 2A and 2B are isometric views of the probe of the thermal airflow tool of FIG. 1 and an enlarged, detailed view of a burning ring in accordance with the principles of the present invention, respectively.

In FIG. 2A, probe 52 is shown as a hollow tube comprising two, electrically conducting half-sections, a negative half-section 34 and a positive half-section 36 insulated from one another by axial cuts 38 extending along most of the length from pressurized air input tube 42 to a burning ring 40 formed on the distal end of probe 52. Two apertures 48, 50 are disposed adjacent to burning ring 40 on opposing sides of the longitudinal axis of probe 52 for advantageously concentrating and directing pressurized air onto a surgical site (see FIG. 9 for example).

Figure 9:
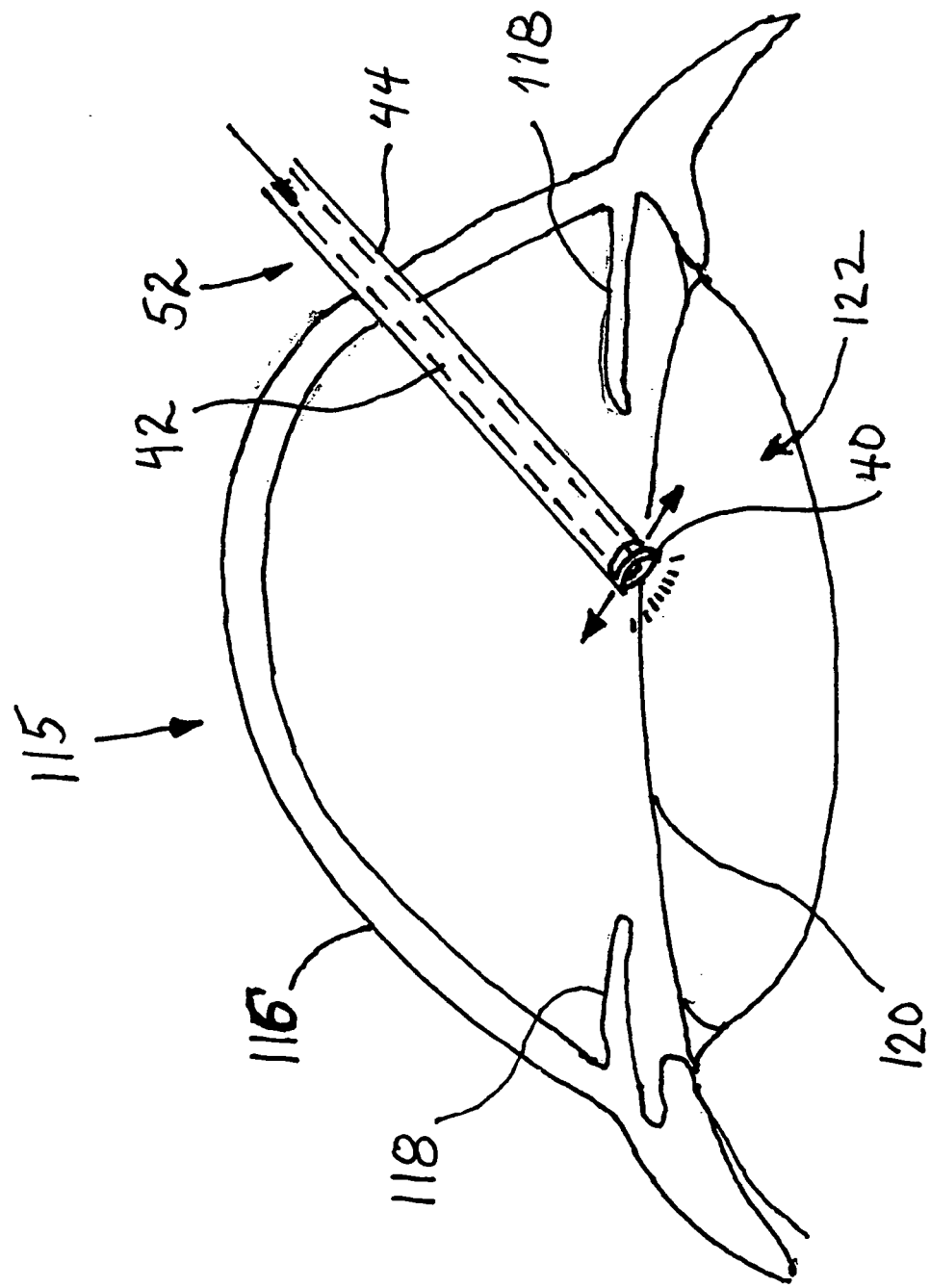
FIG. 9 is a cross-section view of a capsulotomy application of the airflow tool of the invention.

Apertures 48, 50 are formed in a non-perpendicular plane in relation to the axis of probe 52 leaving just a small amount of material which forms neck pieces 49, 51 physically and electrically connecting burning ring 40 with each half-section 34, 36 respectively. Burning ring 40 comprises a thin metal ring obliquely truncated in a plane parallel to the plane of apertures 48, 50 so as to facilitate maximal contact with the surface of a surgical site, such as the spherical surface of an eye when the thermal airflow tool is used in this application (FIG. 9).

Burning ring 40 is heated when an electric current is applied to contact points in electrical contact with burning ring 40 via the two neck pieces 49, 51 which secure burning ring 40 to each of the electrically conducting half-sections 34, 36. Burning ring 40 is fabricated of a heat-conducting material, such as titanium, steel, and the like, which concentrates the heat at the extreme distal edge of probe 52.

FIGS. 3A-D are orthographic views of the hollow tube construction of the probe, and axial cross-sections showing the construction of air pressure release apertures. Probe 52 of the present invention is typically a tubular body, cylindrical in shape, although other shapes are also usable. The interior of this body is lined with a non-conducting, insulating material forming sleeve 44, such as vinyl plastic, or nylon. Air input tube 42 is also made of non-conductive material, such as rubber or plastic (vinyl) and extends slightly outwardly from proximal end of probe 52 to join with air pressure tube 14 (see FIG. 1) connected to air pressure unit 10 (see FIG. 1). Air input tube 42 extends internally along the length of probe 52 to the distal end adjacent to burning ring 40.

Figure 4A:
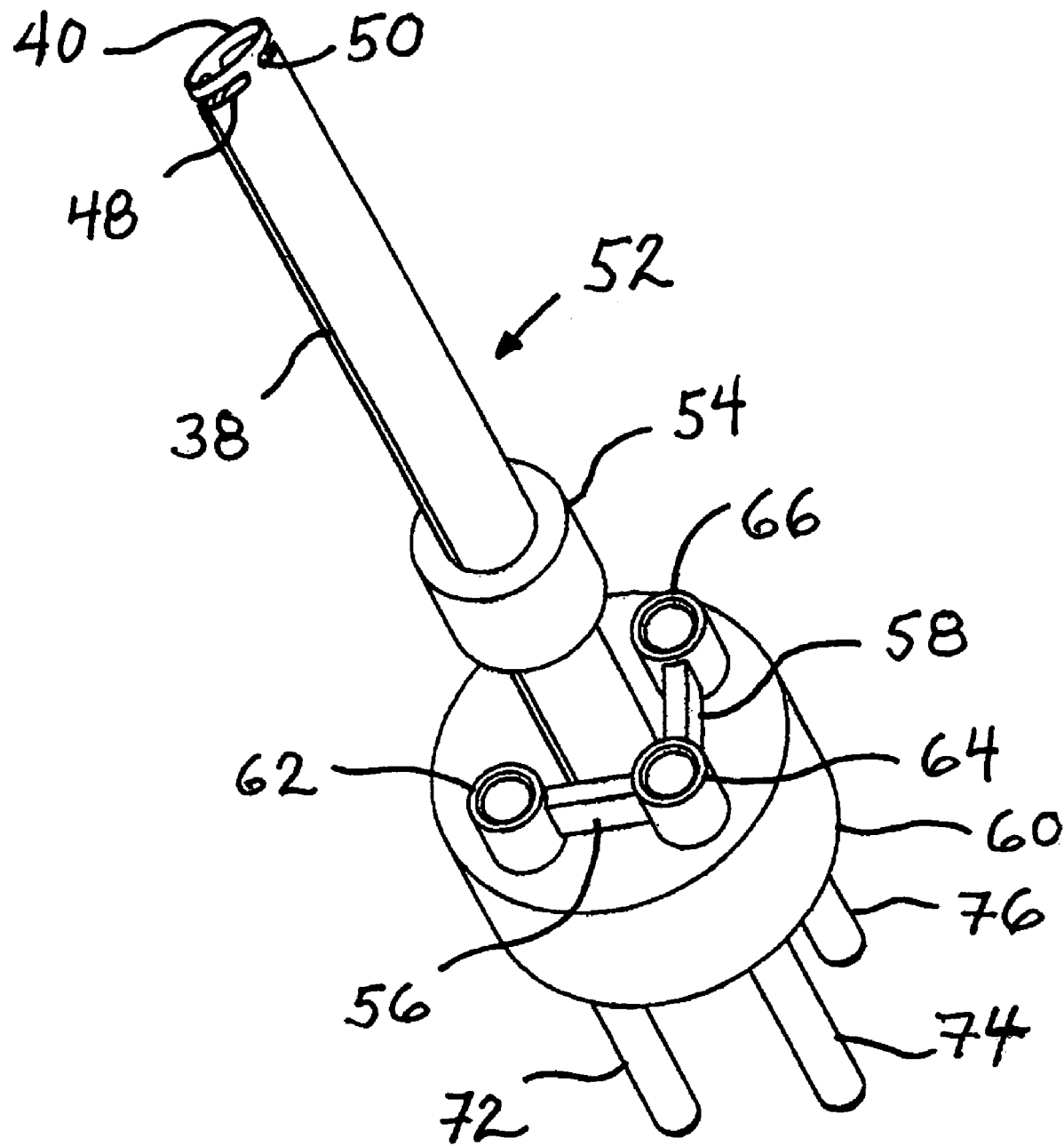
FIG. 4A is an isometric view of a plug-in thermal airflow tool in accordance with an embodiment of the invention.

FIG. 4A is an isometric view of a plug-in thermal airflow tool in accordance with an embodiment of the invention. A non-conductive sleeve 54 retains the two half-sections 34, 36 (see FIG. 2A) at about a mid-portion of probe 52 which is embedded in a non-conductive, three-prong connector base 60 provided with prongs 72, 74, 76 and respective electrical contacts 62, 64, 66 on an inner face of connector base 60. A first resistor 56 and a second resistor 58, in a preferred embodiment of the invention, are provided mounted between contacts 62, 64, and 66 as shown in FIG. 4A. The functions and operation of the circuit is explained below in relation to FIG. 7.

Figure 4B:
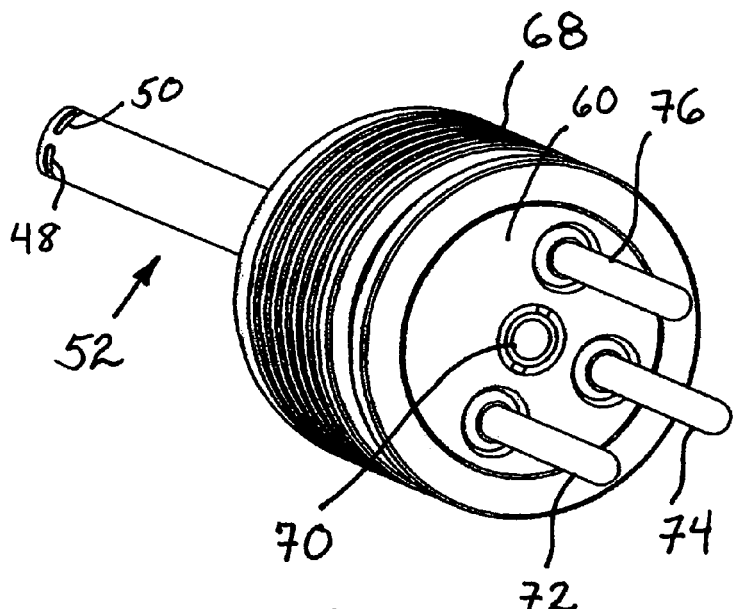
FIGS. 4B and 4C are isometric external views of the plug end and a side view, respectively, of the thermal airflow tool of FIG. 4A shown with a protective housing.
Figure 4C:
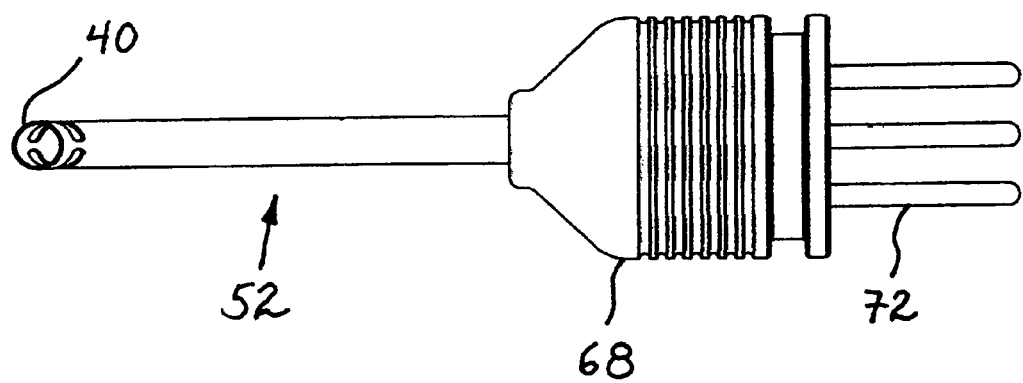

FIGS. 4B and 4C are isometric external views of the plug end and a side view, respectively, of the thermal airflow tool of FIG. 4A shown with a protective housing. The proximal portion of probe 52 is provided with a housing unit 68 for safety of operation and for protecting inner components (see FIG. 4A) mounted on connector base 60. When plugged into a matching female connector (see FIG. 1) mounted in handle 16 (see FIG. 1), the three prongs 72, 74, 76 electrically connect probe 52 to a power source (not shown) within thermal unit 12 (FIG. 1). Note the centrally disposed orifice 70 in the externally oriented face of input connector base 60 to which air input tube 42 (see FIG. 2) is tightly joined when the respective, matching connectors are fully connected.

Figure 5:
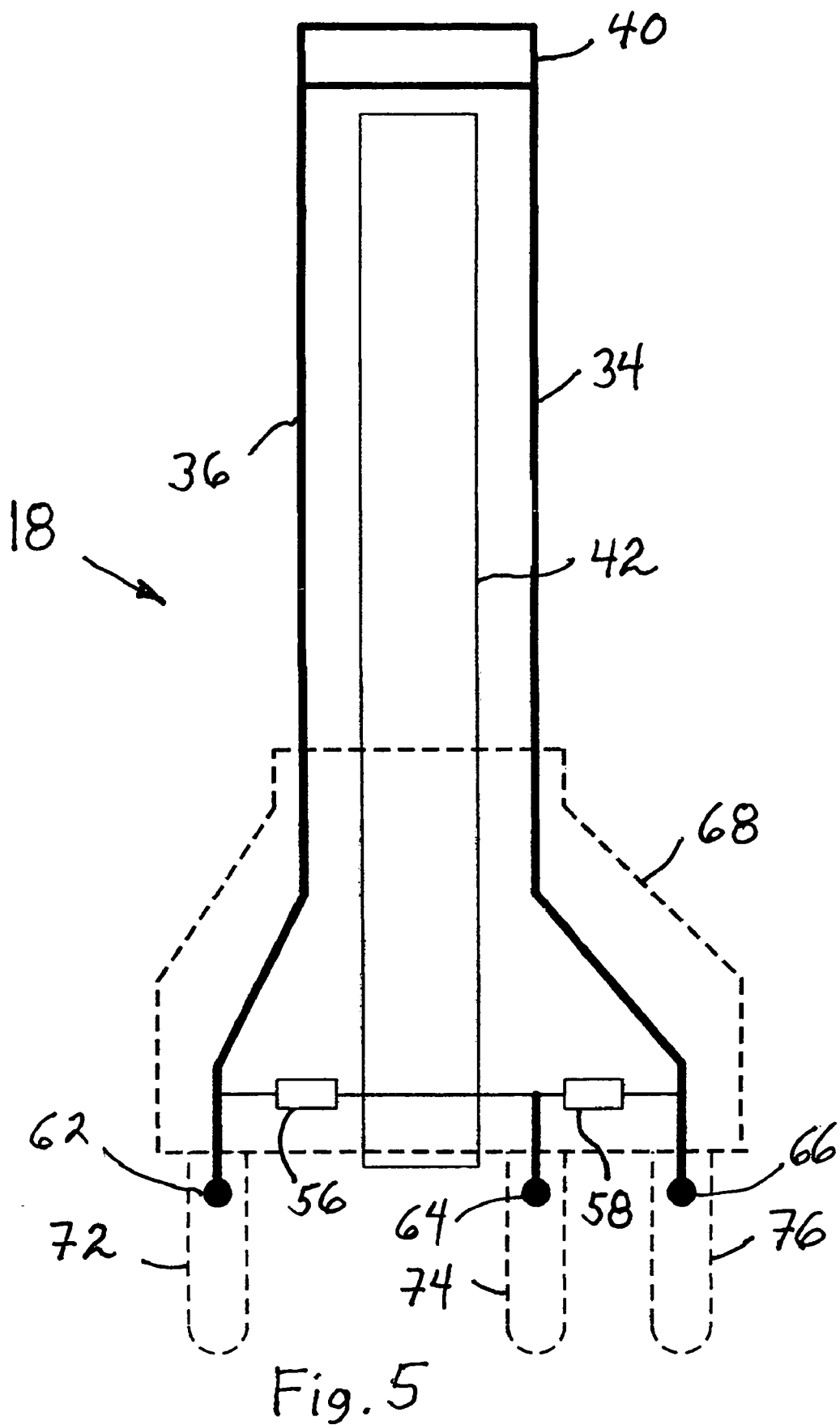
FIG. 5 is a schematic electrical diagram of an embodiment of the invention illustrating a dual-resistor electrical circuit for the airflow tool of FIG. 4A.

FIG. 5 is a schematic electrical diagram of a preferred embodiment of the invention illustrating a dual-resistor electrical circuit for the thermal airflow tool of FIG. 4A.

The two halves 34, 36 of the body of probe 52 serve as positive and negative terminals in relation to one another and burning ring 40. They are wired to the contacts 62, 64, 66 electrically connected to the three prongs 72, 74, 76 mounted in input connector base 60. A reference resistor 56 and a second, burn-out type resistor 58 are mounted between the outer prongs 72, 76 and middle prong 74. The purpose of these resistors 56 and 58 will be explained in the description of the overall electrical operation of the system of the invention given below in reference to FIG. 7.

Burning ring 40 can have different diameters, from 0.5 mm up to several millimeters. If diameters are changed, the current and time frame inputs will be directly affected and result in different parameters for these two factors. To control the heating level of burning ring 40 and protect it from overheating, a calibration resistor 56 in the range of 200 ohms to 18 kilo-ohms in ten steps is inserted between the positive connector 62 and connector 64. A second fuse-type resistor 58 is inserted between connector 64 and connector 66. The values of the burn-out resistor 58 are calibrated in accordance with the size of the diameter of burning ring 40 so as to disable the heating portion of the thermal airflow tool 18 when current flows through the circuit, burning out the second fuse-type resistor 58 once a pre-set temperature is reached. The thermal operation of the airflow tool 18 is thus limited to a single limited-life heating cycle when provided with the fuse-type resistor 58. The thermal airflow tool is conveniently designed to be replaceable for subsequent use by use of a quick release input connector configured with three prongs 72, 74, 76. A matching female connector 22 on the handle 16 (see FIG. 1) provides for quick-release and replacement of the thermal airflow tool.

When a current is applied through electrical power connector 66 and power connector 62 to two points in an angle of 180° of the circumference, burning ring 40 heats up. The duration and power depends on the material used, preferably a titanium alloy, but other alloys are also usable. Titanium is used in a preferred embodiment of the invention due to its advantageous properties of high heat and current resistance.

Figure 6:
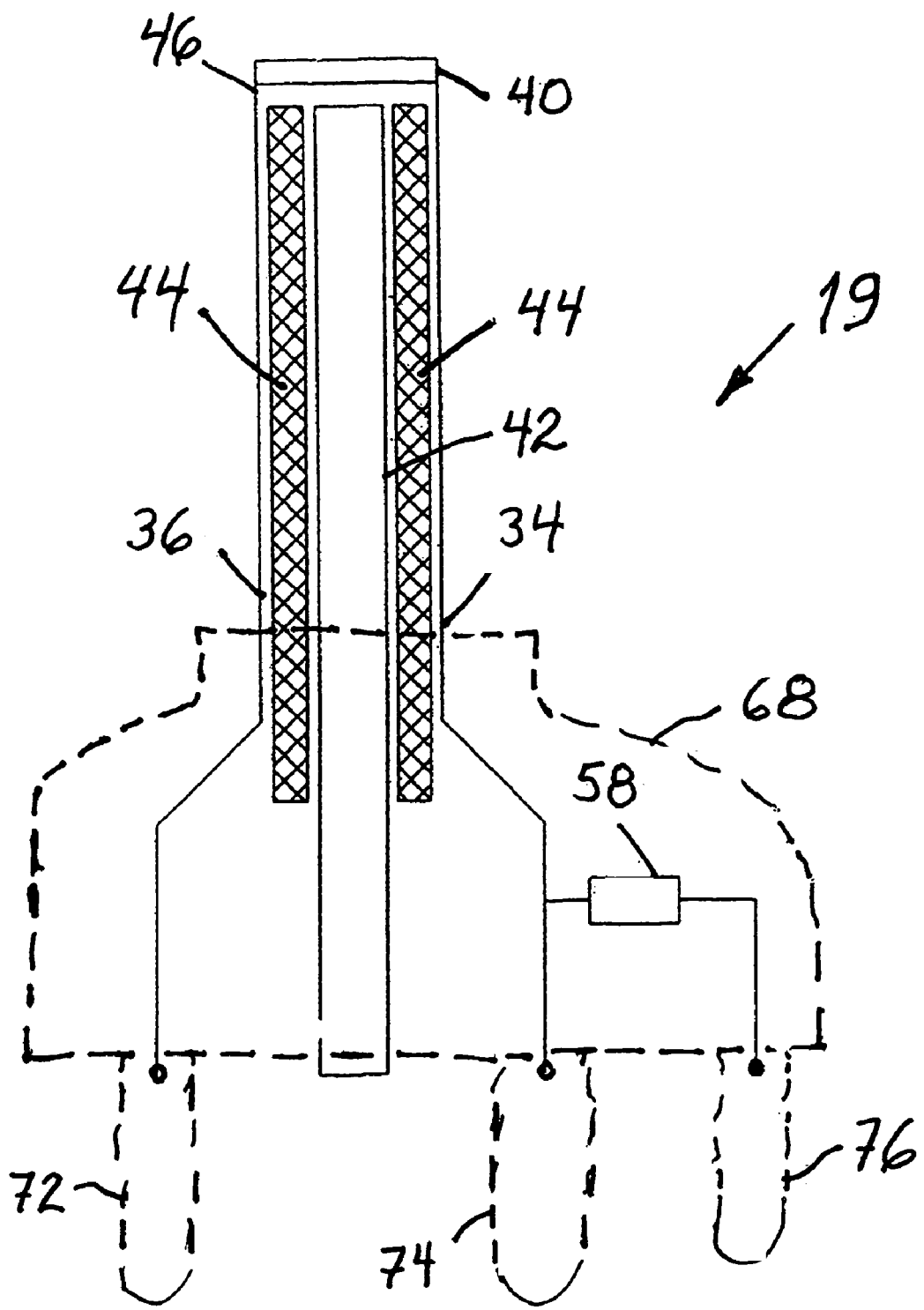
FIG. 6 is a schematic electrical diagram of another embodiment of the invention illustrating a single-resistor electrical circuit for the airflow tool of FIG. 4A.

FIG. 6 is a schematic electrical diagram of another embodiment of the invention illustrating a single-resistor electrical circuit for the thermal airflow tool of FIG. 4A. The effect of using only one resistor 58 is to provide a thermal airflow tool which is reusable if necessary, during one continued surgical procedure on the same patient. The burn-out effect in the use of a dual-resistor thermal airflow tool is not applicable in this embodiment of the invention since the thermal airflow tool continues to function within the pre-set limits of the value of the resistor 58.

Figure 7:
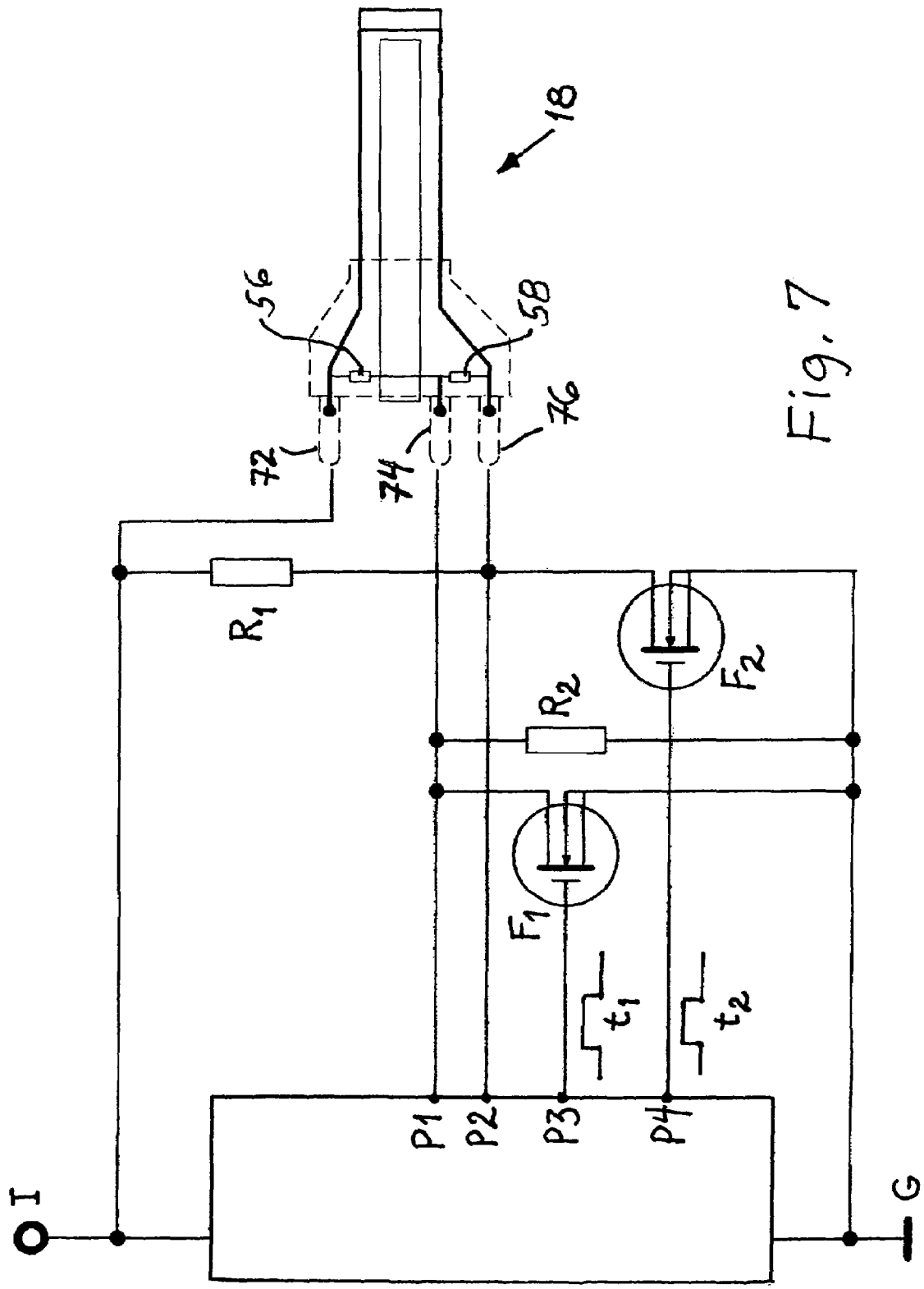
FIG. 7 is a general circuit diagram of the thermal airflow tool of FIG. 4A shown connected electrically to a central processing unit in accordance with the principles of the invention.

FIG. 7 is a general circuit diagram of the thermal airflow tool of FIG. 4B shown connected electrically to a central processing unit in accordance with the principles of the invention.

In an initial test cycle, when a +5 voltage is applied to the circuit at I input, the current flows through prong 72 in the airflow tool 18 and passes through burning ring 40. In parallel, the current passes across a load reference resistor 56 which in a preferred embodiment of the invention is rated at between 1K to about 20K ohms, and which is in electrical connection with resistor $R_2$ rated at about 10K ohms and from there through return at ground G. Pin $P_1$ in microprocessor 84 is activated and reads the voltage applied to the circuit. The fuse-like resistor 58 is determined to be operative if the reading is +5V. However, if the voltage is less than or equal to 4.5V, the fuse-like resistor 58 is not operative. The microprocessor is programmed to start a timer (not shown) for using the thermal power unit 12 for a period over about 10 to 20 minutes. A pulse of time $t_1$, preferably of 100 ms is applied to field effect transistor $F_1$ through pin $P_3$ which promptly kills fuse-resistor 58, that is, makes it inoperative.

A second cycle in the circuit of FIG. 7 tests the reference resistor 56 in airflow tool 18. The input voltage at I is +5V which passes through prong 72 of airflow tool 18 and across reference resistor 56 of the range value 1K to 20K ohms and returns to ground G via middle test-prong 74 and across resistor $R_2$ of 10K ohms. The microprocessor 84 reads the reference resistor 56 whose value is between 1K ohm and 20K ohms in a preferred embodiment of the invention and is set in relation to the diameter of burning head 40. For example: 1K ohm represents a diameter of 1 mm; 2K ohm represents 1.2 mm; and so on, up to 20K ohms which represents 5 mm diameter. Furthermore, a 1K ohm value represents a reference value of 4.5V on pin $P_1$ of microprocessor 84 progressively increasing up to 20K ohms which represents a 2.3V reference value on pin $P_1$.

Finally, the heating cycle for burning ring 40 is activated via microprocessor 84 which switches on field effect transistor $F_2$ over a time $t_2$ set between 10 ms up to 400 ms, in a preferred embodiment of the invention, and which is determined in relation to the diameter of burning ring 40 (read out by the reference resistor 56). Fine adjustment can be made with the potentiometer switch 28 on the front panel of thermal power unit 12.

Figure 8:
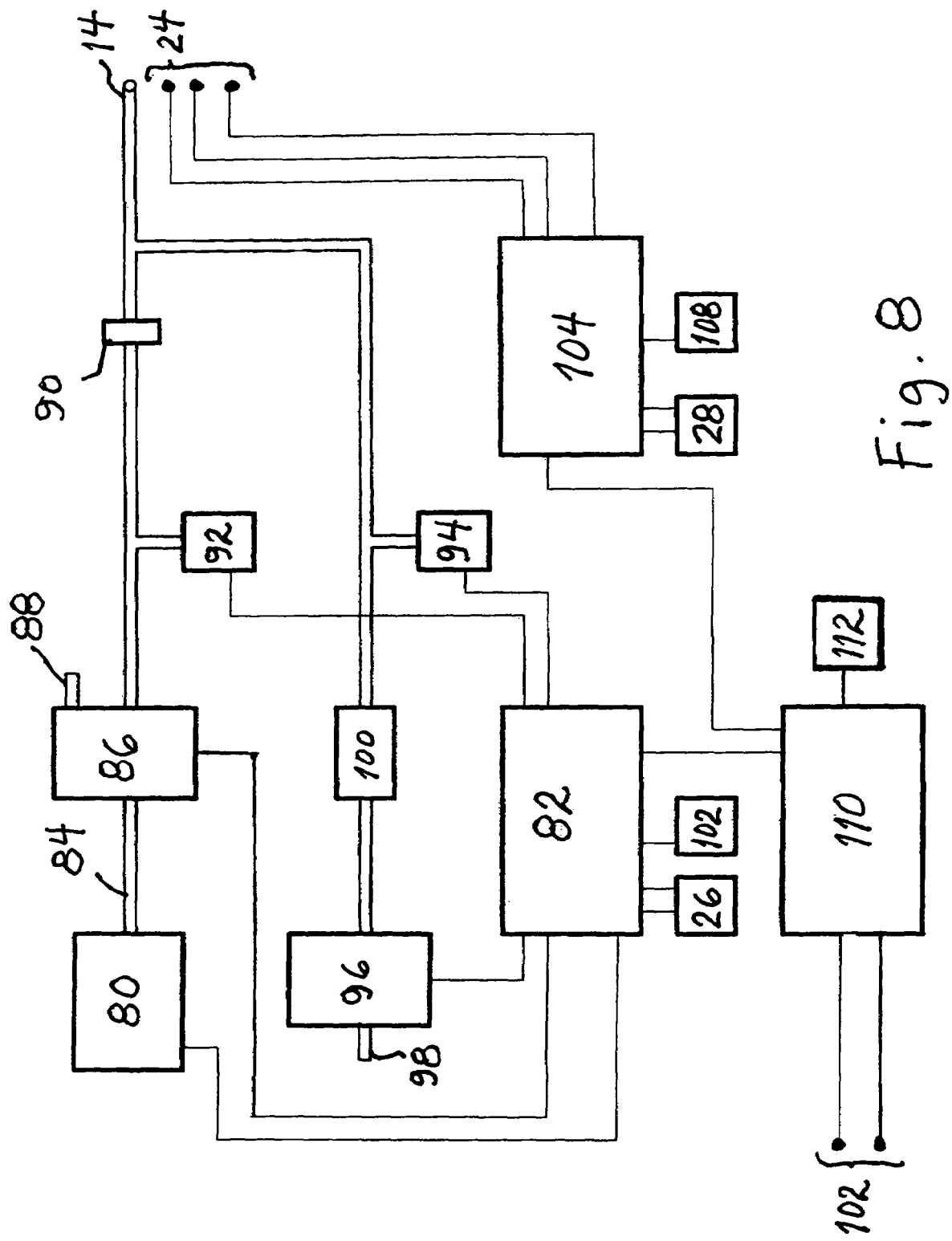
FIG. 8 is a schematic block diagram of an embodiment of the system of the invention.

FIG. 8 is a schematic block diagram of an embodiment of the system of the invention.

A DC-motor-controlled membrane air pump 80 produces the desired air pressure depending on rotation speed. The rotation speed is controlled by the microprocessor 82. On the air pump output 84, a security valve 86 is disposed to rapidly relieve undesirable build-up of air pressure from the system. The valve 86 exhausts the pressurized air under non-current conditions to output 88. The system pressure between the valve 86 and an air filter 90 is checked by a pressure sensor 92 in communication with microprocessor 82. The pressurized air flows out through the air input tube 14 which is connected from air pressure unit 10 to the thermal airflow tool 18 (see FIG. 1). Another flow control pressure sensor 94 is disposed between filter 90 and air input tube 14 which monitors the return air pressure. Sensor 94 checks the return pressure and valve 96 is responsible for the release of overpressure through exhaust 98.

To prevent system swinging, a damping air chamber 100 is disposed between valve 94 and valve 96. Valve 96, in a preferred embodiment of the invention, is a high-speed pulse-width-modulated (PWM) valve chosen for its linear characteristics. The system pressure is pre-selected by control switch 26, which is provided as a potentiometer in a preferred embodiment of the invention, and monitored visually with the aid of a bar graph display 32 (see FIG. 1). A convenient footswitch 102 allows for on and off control of the air flow while freeing the surgeon's hands for necessary manipulation of the thermal airflow tool 18. The thermal unit 12 is controlled for time and power by a second microprocessor 104 and pre-selected by control switch 28 which is provided as a second potentiometer.

While connecting thermal power unit 12 to handle 16 (see FIG. 1), the microprocessor 104 reads out the value of resistor 56 (see FIG. 7) and selects the necessary power range and time. In parallel to the identification resistor 56, a second resistor 58 (see FIG. 7) is provided with a 1 ohm/0.125 W resistance which is blown out (fused) by a starting current. After the second resistor 58 is blown, the microprocessor 104 is able to read out the identification resistor 56. For a much higher identification resistor resistance, it can never be fused. The microprocessor 104 is programmed to allow the user to use the thermal unit 12 for a limited time only. The timer control switch 28, on thermal unit 12 is, in a preferred embodiment of the invention, a second potentiometer, allowing a user to set this time frame.

In an alternate embodiment of the invention, the second resistor 58 is omitted and the airflow tool is consequently reusable, but at a fixed heating level for a given diameter burning ring.

The burning cycle is controlled by microprocessor 104 which is operated by second foot switch 108. The power supply 110, connected to a power source by cable 102, is a standard 110/230 V input and provides a 24V/5V output. An on-off power switch 112 is provided for the power source housed within thermal power unit 12.

FIG. 9 is a cross-section view of a capsulotomy application of the airflow tool of the invention. The thermal airflow tool 52 is inserted through the cornea 116 of an eye 115. Burning ring 40 is carefully moved into close proximity to the anterior surface 120 of the lens 122 which is situated below the iris 118 in the lumen of the eye 115. Pressurized airflow enters probe 52 at the proximal end (shown by arrow) and passes through an inner air input tube 42 (dashed lines) until exiting (indicated by lateral arrows) from distal apertures 48, 50 (see above description and FIGS. 2-3). The pressurized airflow is advantageously dispersed around as well as directed directly onto the surgical site behind the cornea 116 and helps maintain the full configuration of the lumen while simultaneously, burning ring 40 decomposes the target capsule as required. Removal of unwanted substances resulting from the surgery is performed using conventional surgical procedures well-known to those skilled in the art. The use of the thermal airflow tool of the present invention leaves only a tiny hole, perhaps less than three millimeters in diameter, in the cornea and saves making larger incisions in the eye which might take longer to heal and cause complications.

Having described the invention with regard to certain specific embodiments, it is to be understood that the description is not meant as a limitation, since further modifications may now suggest themselves to those skilled in the art, and it is intended to cover such modifications as fall within the scope of the invention.

The invention claimed is:

1. A thermal airflow tool for performing a thermal surgical procedure on a surgical site having a structural configuration requiring maintenance thereof during said procedure, said thermal airflow tool comprising:
 a probe comprising:
 an elongated, hollow body adapted to provide electrical power to a burning ring formed at a distal end thereof, wherein said burning ring is adapted to contact the surface of a surgical site to form an orifice with a predetermined diameter,
 wherein two axial cuts extend along the majority of the length of said probe, dividing said probe into a negative half-section and a positive half-section insulated from one another by said axial cuts;
 an air channel for conducting pressurized airflow to said distal end of said probe;
 at least two apertures radially disposed at said distal end of said probe in a non-perpendicular plane in respect to the axis of said hollow body,
 said apertures being formed integral with the distal end of said axial cuts being shaped for release of said pressurized airflow wherein said airflow is adapted to be directed onto the surgical site to help in maintaining the structural configuration associated with a body part undergoing surgery,
 said air channel and said at least two apertures being in physical communication with one another within said hollow body of said probe; and
 an input connector mounted on a proximal end of said probe for connecting said probe with respective sources of said electrical power and said pressurized airflow, said input connector having at least one resistor for controlling and monitoring the electrical power provided to said burning ring.

2. A thermal airflow tool for performing a thermal surgical procedure, said thermal airflow tool comprising:
 a probe having an elongated body, wherein two axial cuts extend along the majority of the length of said probe, dividing said probe into a negative half-section and a positive half-section insulated from one another by said axial cuts,
 said elongated body being adapted to provide electrical power to a burning ring formed at a distal end thereof, wherein said burning ring is formed at an oblique angle from said elongated body, for formation of a burn having a diameter larger than the diameter of the hollow body, as measured along the largest axis of the burn;
 an input connector mounted on a proximal end of said probe for connecting said probe with an electrical power source, said input connector having at least one resistor in an electrical circuit for controlling and monitoring the electrical power provided to said burning ring, and
 an air channel for conducting pressurized airflow to said distal end of said probe;
 at least two apertures radially disposed at said distal end of said probe in a non-perpendicular plane in respect to the axis of said hollow body, said apertures being formed integral with the distal end of said axial cuts being shaped for release of said pressurized airflow,
 wherein said airflow is adapted to be directed onto the surgical site to help in maintaining the structural configuration associated with a body part undergoing surgery,
 and wherein application of electrical current to said tool results in concentration of heat at the distal end of said probe.

3. The tool of claim 2, wherein an air channel is present for conducting pressurized airflow to said distal end of said probe, said body of said probe is hollow, and
 at least two apertures are radially disposed at said distal end of said probe in a non-perpendicular plane in respect to the axis of said hollow body for release of said pressurized airflow, said air channel and said at least two apertures being in physical communication with one another within said hollow body of said probe; and said input connector connects said probe with a pressurized airflow source.

4. The tool of claim 3, wherein said air channel is formed from an electrically insulating material such as vinyl, plastic and nylon.

5. The tool of claim 2, wherein said burning ring is formed of a heat-conducting material such as titanium and steel.

6. The tool of claim 2, wherein the interior of said probe is lined with an electrically insulating material forming a sleeve.

7. The tool of claim 6, wherein said material is such as vinyl, plastic and nylon.

8. The tool of claim 2, wherein said resistor is a calibration resistor for controlling the heating level of said burning ring and protecting said burning ring from overheating.

9. The tool of claim 8, wherein said calibration resistor is a ten step calibration resistor, in the range of 200 ohms to 18 kilo-ohms, inserted between a positive connector and a second connector.

10. The tool of claim 8, wherein said tool is reusable.

11. The tool of claim 8, further comprising a burn-out fuse-type resistor, which burns out when a pre-set temperature is reached, for limiting the operation of the airflow tool to a single use.

12. The tool of claim 2, wherein said burning ring is provided with a diameter within the range of 0.5 millimeters, to several millimeters.

13. The tool of claim 2, wherein said input connector comprises a non-conductive, three-prong connector base provided with prongs and respective electrical contacts on an inner face of said connector base.

14. The tool of claim 2, wherein said an input connector can releasably mate with an electrical power source.

15. The tool of claim 2, wherein said tool is disposable.

16. The tool of claim 2, wherein said pressurized airflow has substantially linear characteristics.

17. A system for performing a thermal surgical procedure, comprising:
 a probe having an elongated body, wherein two axial cuts extend along the majority of the length of said probe, dividing said probe into a negative half-section and a positive half-section insulated from one another by said axial cuts,
 said elongated body being adapted to provide electrical power to a burning ring formed at a distal end thereof, wherein said burning ring is formed at an oblique angle from said elongated body, for formation of a burn having a diameter larger than the diameter of the body, as measured along the largest axis of the burn;
 an input connector mounted on a proximal end of said probe for connecting said probe with an electrical power source, said input connector having at least one resistor for controlling and monitoring the electrical power provided to said burning ring,
 an electrical power supply for providing electrical power to said system; and an air channel for conducting pressurized airflow to said distal end of said probe;

at least two apertures radially disposed at said distal end of said probe in a non-perpendicular plane in respect to the axis of said hollow body, said apertures being formed integral with the distal end of said axial cuts being shaped for release of said pressurized airflow wherein said airflow is adapted to be directed onto the surgical site to help in maintaining the structural configuration associated with a body part undergoing surgery, and wherein application of electrical current to said tool results in concentration of heat at the distal end of said probe.

18. The system of claim 17, further comprising an air pressure unit for providing said pressurized airflow having substantially linear characteristics to said probe.

* * * * *